United States Patent [19]
Longo et al.

[11] Patent Number: 5,670,359
[45] Date of Patent: Sep. 23, 1997

[54] CLONED NSII RESTRICTION-MODIFICATION SYSTEM

[75] Inventors: Mary C. Longo, Germantown; Michael D. Smith, Rockville, both of Md.

[73] Assignee: Life Technologies, Inc., Rockville, Md.

[21] Appl. No.: 563,266

[22] Filed: Nov. 27, 1995

Related U.S. Application Data

[63] Continuation of Ser. No. 145,518, Nov. 4, 1993, Pat. No. 5,470,740.

[51] Int. Cl.$^6$ .................................................... C12N 9/22
[52] U.S. Cl. ..................... 435/199; 435/193; 435/320.1; 536/23.2
[58] Field of Search .......................... 435/199, 193, 435/320.1; 536/23.2

[56] References Cited

U.S. PATENT DOCUMENTS

| | | | |
|---|---|---|---|
| 5,082,784 | 1/1992 | Chatterjee et al. | 435/252.3 |
| 5,179,015 | 1/1993 | Wilson et al. | 435/172.3 |
| 5,192,675 | 3/1993 | Chatterjee et al. | 435/199 |
| 5,200,333 | 4/1993 | Wilson | 435/172.3 |
| 5,312,746 | 5/1994 | Longo et al. | 435/193 |

OTHER PUBLICATIONS

Brooks, J., "Cloning the BamHI restriction modification system", *Nucl. Acids Res.* 17:979–997 (1989).
Gibco BRL Catalogue, p. 253 (1992).
Hammond, A., "Cloning the KpnI restriction–modification system in *Escherichia coli*", *Gene* 97:97–102 (1990).
Heitman, J., "Site–Specific Methylases Induce the SOS DNA Repair Response in *Escherichia coli*", *J. of Bacteriology* 169:3243–3250; (Jul., 1987).
Life Technologies Catalogue, pp. 6–32 (1993–1994).
Lunnen, K., "Cloning type–II restriction and modification genes", *Gene* 74:25–32 (1988).
Raleigh, E., "*Escherichia coli* K–12 restricts DNA containing 5–methylcytosine", *Proc. Natl. Acad. Sci.* 83:9070–9074 (Dec. 1986).
Reddy, P., "Hyperexpression and purification of *Escherichia coli* adenylate cyclase using a vector designed for expression of lethal gene products", *Nucl. Acids Res.* 17:10473–10488 (1989).
Revel, H., "Restriction of Nonglucosylated T–even Bacteriophage: Properties of Permissive Mutants of *Escherichia coli* B and K12$^1$", *Virology* 31:688–701 (1967).
Robert, R., "Restriction enzymes and their isoschizomers", *Nucl. Acids Res.* 17:r347–r387 (1989).
Wilson, G., "Organization of restriction–modification systems", *Nucl. Acids Res.* 19:2539–2566 (1991).
Howard, K., "Cloning the DdeI restriction–modification system using a two–step method" *Nucl. Acids Res.* 14:7939–7951 (1986).

*Primary Examiner*—Charles L. Patterson, Jr.
*Attorney, Agent, or Firm*—Sterne, Kessler, Goldstein & Fox P.L.L.C.

[57] ABSTRACT

The present invention discloses the cloning and expression in *Escherichia coli* of the NsiI restriction-modification system from *Neisseria sicca*, utilizing a two step protocol. Initial protection of the *E. coli* host with methylase expressed on a plasmid was required to stabilize a compatible plasmid carrying the endonuclease gene on a single DNA fragment. A chromosomal map was generated localizing the genes for NsiI methylase and endonuclease. An *E. coli* strain was constructed which produced high levels of NsiI endonuclease.

15 Claims, 3 Drawing Sheets

CLONED NSII RESTRICTION-MODIFICATION SYSTEM

This application is a continuation of application Ser. No. 08/145,518, filed Nov. 4, 1993, now U.S. Pat. No. 5,470, 740.

FIELD OF THE INVENTION

The present invention is in the field of genetic engineering and molecular biology. It concerns production of proteins, specifically the restriction endonuclease NsiI, in a heterologous organism from a gene carried by a recombinant DNA molecule.

BACKGROUND OF THE INVENTION

There has been much effort to clone restriction-modification systems. The first cloning of a DNA endonuclease gene was described by Mann M B et al. (1978) *Gene* 3:97–112. Since then more than seventy DNA methylase and restriction endonucleases have been cloned, the majority of the restriction endonuclease genes being closely linked to its corresponding methylase gene. Cloning of such genes allows one to produce large quantities of an enzyme.

Several methods by which restriction-modification systems can be cloned have been described. A number of endonuclease and methylase genes have been cloned from endogenous plasmids: EcoRII (Kosykh V B et al. (1980) *Mol. Gen. Genet.* 178:717–718), EcoRI (Newman A K et al. (1981) *J. Biol. Chem.* 256:2131–2139, Greene P J et al. (1981) *J. Biol. Chem.* 256:2143–2153), EcoRV (Bougueleret L et al. (1984) *Nucl. Acids Res.* 12:3659–3676), PvuII (Blumenthal R M et al. (1985) *J. Bacteriol.* 164:501–509), and PaeR71 (Gingeras T R and Brooks J E (1983) *Proc. Natl. Acad. Sci. USA* 80:402–406). Other methods of cloning include a phage restriction method in which bacterial cells carrying cloned restriction and modification genes will survive phage infection (Mann et al. supra; Walder R Y et al. (1981) *Proc. Natl. Acad. Sci. U.S.A.* 78:1503–1507; Rodicio M R and Chater K F (1988) *Mol. Gen. Genet.* 213:346–353), and a procedure based on methylation protection suggested by Mann et al., supra, and Szomolanyi E et al. (1980) *Gene* 10:219–225. This latter scheme involves digestion of a plasmid library with the restriction enzyme to be cloned so that only plasmids whose sequences are modified, because of the presence of the methylase, will produce transformants in a suitable host. This selection has worked well to clone endonuclease and methylase genes together as well as methylase genes alone (Szomolanyi et al., supra; Janulaitis A et al. (1982) *Gene* 20:197–204; Walder R Y et al. (1983) *J. Biol. Chem.* 258:1235–1241; Kiss A and Baldanf F (1983) *Gene* 21:111–119; Wilson G G (1988) *Gene* 74:281–289). However, this technique sometimes yields only the methylase gene, even though the endonuclease and modifying genes are closely linked.

Cloning of certain restriction-modification systems in *E. coli*, including DdeI (Howard K A et al. (1989) *Nucl. Adds Res.* 14:7939–7950), BamHI (Brooks J E et al. (1989) *Nucl. Acids Res.* 17:979–997), KpnI (Hammond A W et al. (1990) *Gene* 97: 97–102), ClaI (U.S. application Ser. No. 08/002, 032) and NsiI (disclosed herein), has required a multi-step approach. In each case, protection of the host with methylase expressed on a plasmid was necessary to stabilize a compatible vector containing the functional endonuclease gene. It would appear that in these cases, simultaneous introduction of the methylase and endonuclease genes results in degradation of the cell genome because the endonuclease is able to cleave the unmodified sites before the methylase is able to protect them. If the methylase is already in the cell at the time the endonuclease gene is introduced, there should be no unmodified sites and the endonuclease gene is not toxic.

SUMMARY OF THE INVENTION

The present invention relates to isolated DNA coding for the NsiI restriction endonuclease.

The invention also relates to a vector which comprises a structural gene coding for the NsiI restriction endonuclease.

The invention also relates to a method of producing NsiI restriction endonuclease comprising, in series, the steps of (a) growing a cell protected from NsiI cleavage and transformed with the vector of the invention under conditions suitable for the expression of said endonuclease; and (c) isolating the NsiI endonuclease.

The invention also relates to a method of using the vector of the invention to prepare an NsiI restriction endonuclease, comprising:

(a) introducing said vector into a host cell to produce a recombinant host cell;

(b) culturing said recombinant host cell; and (c) isolating said restriction endonuclease from said recombinant host cell.

The invention also relates to a substantially pure enzyme obtained by the process of the invention.

The invention also relates to a recombinant host cell comprising an NsiI endonuclease structural gene, wherein the cell is not of the genus Neisseria.

In particular, the present invention relates to the cloning and expression in a transformed host cell the NsiI restriction-modification system utilizing a two-step protocol. Initial protection of *E. coli* by methylase was required for the establishment of a plasmid containing the NsiI restriction and modification genes on a common fragment.

The genes encoding the NsiI restriction and modification system from *Neisseria sicca* were cloned and expressed in *Escherichia coli*. The NsiI restriction endonuclease recognizes and cuts the sequence 5' ATGCA^T 3' ("^" indicates the site of cutting); the exact specificity of the NsiI methylase is unknown. Although the endonuclease and methylase genes were linked, initial attempts using a prior art method to clone both genes as a single DNA fragment in a plasmid vector isolated deletions spanning all or part of the gene coding for the restriction enzyme. Initial protection of the *E. coli* host with methylase expressed on a plasmid was required to stabilize a compatible plasmid carrying both the endonuclease and the methylase genes on a single DNA fragment. A chromosomal map was generated localizing the genes for NsiI methylase. An *E. coli* strain, DH10BRec+/pSUM83/pUC123, was constructed which contained two compatible plasmids: a plasmid carrying the NsiI endonuclease gene (pUC123), and a second plasmid expressing NsiI methylase (pSUM83). This strain produces approximately twenty thousand units of NsiI endonuclease per gram wet weight of cells. This is approximately one third of the level of NsiI produced by *N. sicca*, but the *E. coli* cells are easier to grow than the *N. sicca* strain, and it is expected that the endonuclease will be easier to purify.

site in pCP13 is the lambda packaging site. "amp" is the ampicillin resistance determinant, "kan" is the kanamycin resistance determinant, lacZ' is the gene for the alpha peptide of β-galactosidase.

Figure 1:
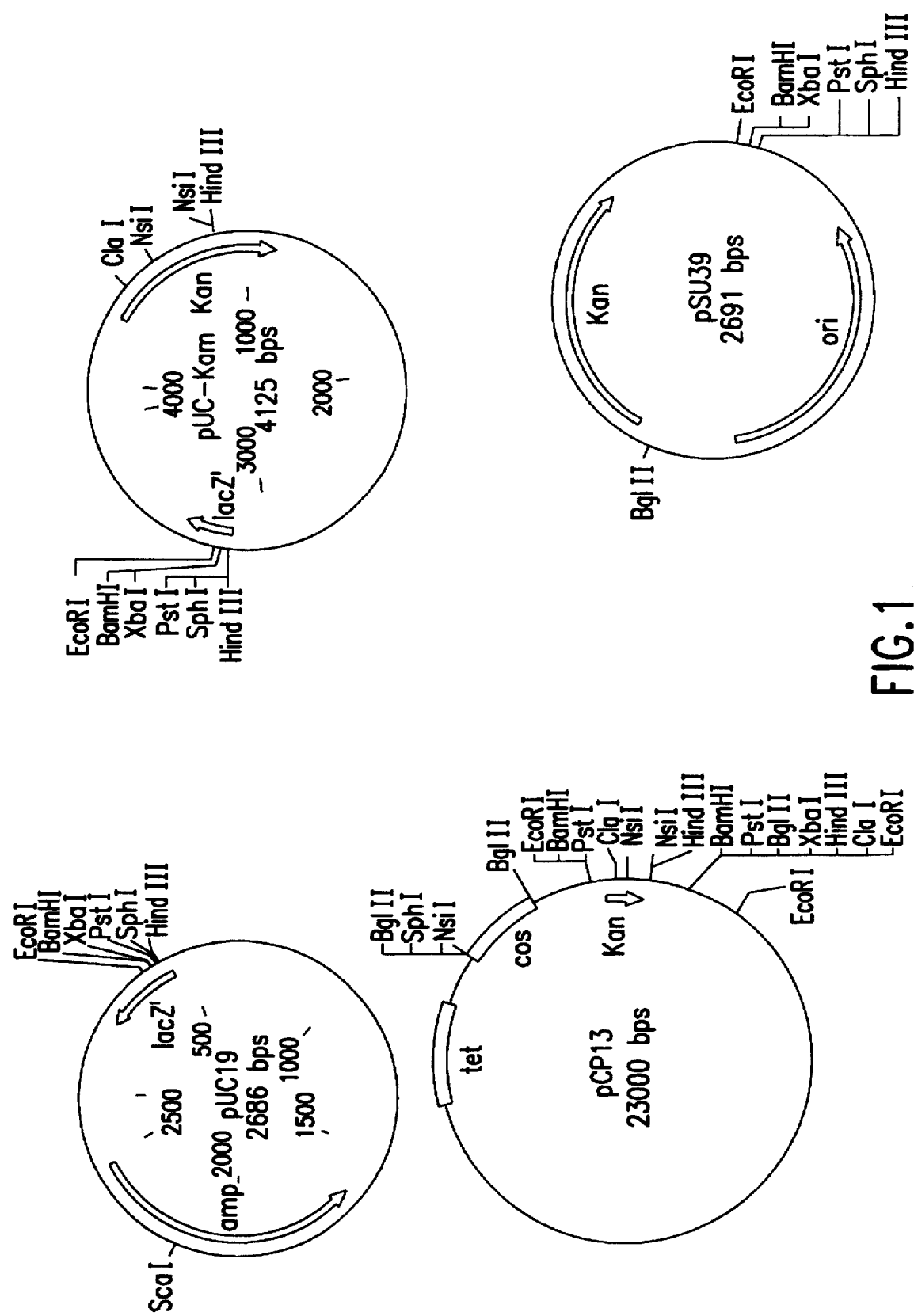
FIG. 1 presents the plasmid maps of cloning vectors pCP13, pUC19, pUC-Kam and pSU39 used in the experiments. Plasmid circles are not all in the same scale. "cos"
Figure 2:
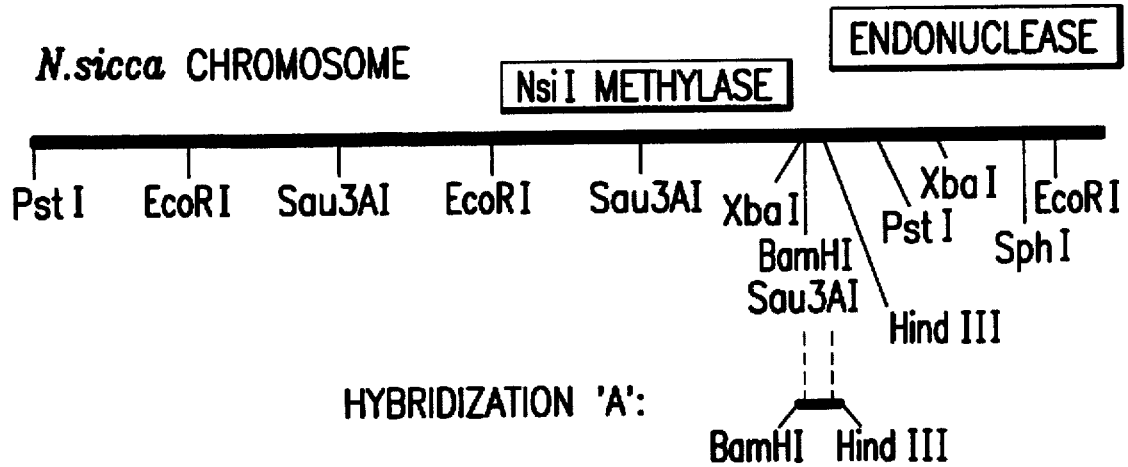
Figure 2:
Figure 2:
Figure 2:
Figure 2:

FIG. 2 presents the hybridization map of the *N. sicca* chromosome in the area of the NsiI restriction-modification system and the corresponding inserts in the clones derived from this region. A probe (probe "A") was generated from pUCKamM1 by cleaving the plasmid with HindIII and BamHI, isolating the 400 base pair fragment, and labeling it with biotin. The BamHi sites are also Sau3AAI sites. In pUCKamM33, the right end of the insert was from the BamHI(Sau3AI) site in pUCKamM1, thus the *N. sicca* DNA in the insert ends at the PstI site.

Figure 3:
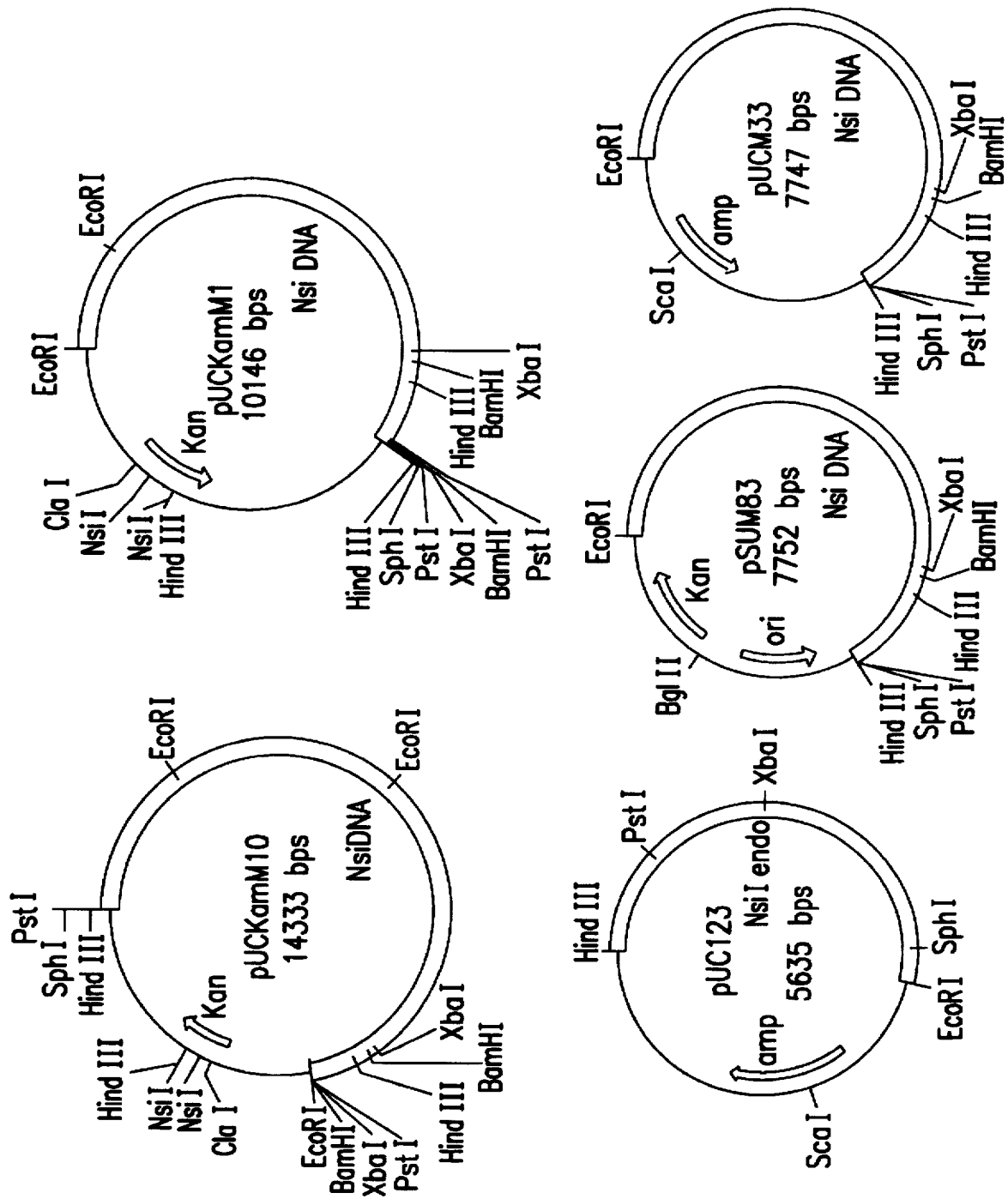

FIG. 3 presents the plasmid maps of pUCKamM1, pUCM33, pSUM33 and pUC123. NsiI methylase clones such as pCPM4 are pCP13 derivatives which is about 49 kb in length, were not mapped, and are not shown in the Figure.

DETAILED DESCRIPTION OF THE PREFERRED EMBODIMENTS

Definitions

In the description that follows, a number of terms used in recombinant DNA technology are utilized extensively. In order to provide a clear and consistent understanding of the specification and claims, including the scope to be given such terms, the following definitions are provided.

Cloning vector. A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression vector. A vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

Substantially pure. As used herein means that the desired purified enzyme is essentially free from contaminating cellular components, said components being associated with the desired enzyme in nature, as evidenced by a single band following polyacrylamide-sodium dodecyl sulfate gel electrophoresis. Contaminating cellular components may include, but are not limited to, phosphatases, exonucleases or other undesirable endonucleases.

Restriction endonuclease isoschizomer. A restriction endonuclease isoschizomer is a term used to designate a group of restriction endonucleases that recognize and bind to the same recognition sequence but are isolated from different microbial sources. Restriction endonuclease isoschizomers may or may not cleave in the exact location as the restriction endonuclease with which it is being compared.

Modification methylase isoschizomer. A modification methylase isoschizomer is a term used to designate a group of modification methylases that recognize the same recognition sequence but are isolated from different microbial sources. Modification methylase isoschizomers may or may not chemically modify the same nucleotides within the recognition sequence as the restriction endonuclease with which it is being compared.

Recognition sequence. Recognition sequences are particular DNA sequences which a restriction endonuclease or a modification methylase recognizes and binds. Recognition sequences are typically four to six (and in some cases, eight) nucleotides in length with a two-fold axis of symmetry.

Recombinant Host. According to the invention, a recombinant host may be any prokaryotic or eukaryotic microorganism which contains the desired cloned genes on an expression vector or cloning vector. This term is also meant to include those microorganisms that have been genetically engineered to contain the desired gene(s) in the chromosome or genome of that organism. The term "recombinant host" is not meant to include the wild type Neisseria strain which produces NsiI.

Recombinant vector. Any cloning vector or expression vector which contains the desired cloned gene(s).

Host. Any prokaryotic or eukaryotic microorganism that is the recipient of a replicable expression vector or cloning vector. A "host," as the term is used herein, also includes prokaryotic or eukaryotic microorganisms that can be genetically engineered by well known techniques to contain desired gene(s) on its chromosome or genome. For examples of such hosts, see Maniatis et al., *Molecular Cloning: A Laboratory Manual*, Cold Spring Harbor Laboratory, Cold Spring Harbor, New York (1982).

Promoter. A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter.

Gene. A DNA sequence that contains information needed for expressing a polypeptide or protein.

Structural gene. A DNA sequence that is transcribed into messenger RNA (mRNA) that is then translated into a sequence of amino acids characteristic of a specific polypeptide.

Expression. Expression is the process by which a polypeptide is produced from a structural gene. The process involves transcription of the gene into mRNA and the translation of such mRNA into polypeptide(s).

Nomenclature for naming restriction endonucleases are in accord with the proposal of Smith et al., *J. Mol. Biol.* 81:419–423 (1973). Briefly, the first letter "N" of NsiI designates the genus "Neisseria" while the lower case letters "si" designate the species "*sicca.*" Thus, the original strain found to produce NsiI was designated *Neisseria sicca* ("BRL 397").

This invention is directed to recombinant hosts which express the gene coding for the restriction endonuclease NsiI and to DNA molecules which contain the gene.

This present invention is further directed to gene(s) coding for the modification methylase genes which are complementary to the NsiI restriction endonuclease. These methylases chemically modify certain nucleotides with the recognition sequence by the addition of a methyl group, thus making the modified sequence resistant to cleavage by the complementary restriction endonuclease.

Also provided by this invention are recombinant hosts and DNA molecules which contain genes coding for isoschizomers of the restriction endonuclease and modification methylase of the present invention. Methods for producing the enzymes of the invention are also disclosed.

The restriction endonuclease NsiI and its corresponding modification methylase may be obtained from any strain of N. sicca. Genes coding for isoschizomers of these enzymes can be obtained from any genus including, but not limited to, Arthrobacter, Bacillus, Citrobacter, Enterobacter, Escherichia, Flavobacterium, Caryophanon, Klebsiella, Micrococcus, Xanthomonus, Nocardia, Pseudomonus, Salmonella, and Streptomyces. The preferred genus to isolate isoschizomers of the restriction endonuclease of the present invention is Neisseria.

DNA molecules which code for NsiI and NsiI methylase, or isoschizomers thereof, can be recombined into a cloning vector and introduced into a host cell to enable the expression of the restriction endonuclease or modification methylase by that cell. DNA molecules may be recombined with vector DNA in accordance with conventional techniques, including restriction digestion to provide appropriate termini, filling in of cohesive ends as appropriate, alkaline phosphatase treatment to avoid undesirable joining, and ligation with appropriate ligases.

The chosen method for cloning restriction endonuclease genes and genes of their DNA-protecting methylases relies on the proximity of the two genes to each other and on the expression of both genes in E. coli. One makes a library of DNA from the source organism in an E. coli vectors. For this library, one chooses a vector having one or, preferably more cleavage sites of the restriction enzyme one wishes to clone. One generally uses partial digestion conditions to prepare the library inserts, so that one avoids always cutting in the middle of a gene. After this library has been transformed into and grown in E. coli, DNA is isolated from uncloned cells. The DNA isolated is a mixture of different molecules, having virtually all possible inserts. The vector/insert combinations having a methylase gene will have methylated endonuclease cleavage sites if the methylase is expressed in E. coli. One then digests the isolated DNA with the restriction enzyme. Unmethylated vector/insert combinations are degraded and methylated combinations survive the endonuclease treatment. The endonuclease-treated DNA is then transformed into E. coli. Degraded combinations do not become established. Methyl-protected combinations, which survived the endonuclease treatment, can establish and maintain themselves in the new E. coli host cells, thereby forming clones. Cell extracts of these clones are then assayed for restriction endonuclease activity, thus identifying clones expressing the restriction enzyme. Thus genes for a restriction methylase and endonuclease system can be cloned on a single recombinant DNA molecule, the restriction endonuclease being used to select DNA molecules carrying the gene of its methylase.

There are a number of reasons why the above method might not work with a particular endonuclease/methylase system. (1) The two genes may not be closely linked. In that case the two genes cannot be on the same DNA fragment insert. (2) The cloned fragment may, by chance, contain only the methylase gene. A closely linked endonuclease gene might be inactivated by being cut by the restriction enzyme that generated the fragment. Similarly the methylase and endonuclease genes may have been separated from each other by a cut at an intervening restriction site. (3) The level of expression of the endonuclease may be high relative to the expression level of the methylase. In this situation, before the expressed methylase can protect DNA, the expressed endonuclease destroys the vector/insert combination and/or kill the host cell by degrading its chromosome(s). (4) The methylase gene may not be expressed in the new host, leading to lack of protection of DNA from the nuclease. (5) The endonuclease gene may not be expressed in the new host.

Another approach for cloning a restriction enzyme gene is to isolate the protein, obtain an amino acid sequence for at least a portion of it, derive a corresponding nucleic acid sequence, synthesize a nucleic acid probe having the latter sequence, and using that probe to clone the gene. This is far more laborious than the standard method. In situations (1) and (3), if the endonuclease is expressed there will be no methylase enzyme to protect DNA in the host cell and the attempt to clone the endonuclease would fail.

The present invention is based on the discovery that for the NsiI restriction/modification system the usual methods for cloning restriction system genes do not work. By analyzing the chromosome of N. sicca by hybridization, we discovered that the NsiI methylase genes in our first libraries were in DNA contexts that were different from the context of the NsiI methylase gene in the N. sicca chromosome. We hypothesized that the NsiI endonuclease gene was closely linked to the NsiI methylase gene in the N. sicca chromosome but that the endonuclease gene was toxic to the host. In this case, the only clones which would survive would be those in which the NsiI methylase was unlinked to the endonuclease gene by some kind of rearrangement. We further hypothesized that an intact clone of the NsiI endonuclease and methylase genes may be obtained if NsiI methylase was present in the heterologous host before introducing the library. In order to detect the desired transformants, we needed a probe for N. sicca DNA which is closely linked to the NsiI methylase gene, but is not present on the NsiI methylase plasmid which is protecting the cell. Despite using several restriction enzymes to map the region, we found that such a sequence was not available, and that the only sequence we could use was over 4 kb from the desired sequence. We then devised a method by which we could clone the endonuclease gene in a host protected by the NsiI methylase without using colony hybridization at all.

The overall strategy for reproducing this invention is as follows. One isolates DNA from a NsiI producing strain of N. sicca, exemplified herein with BRL 397. BRL 397 is on deposit at the American Type Culture Collection, 12301 Parklawn Drive, Rockville, Md. 20852, as ATCC 29256. One then makes a recombinant DNA library, transforms that library into a host, preferably E. coli, and isolates bulk insert/vector DNA combinations of that library from host cells. A portion of this DNA library is then digested with NsiI. The resulting mixture is then transformed into fresh host cells. Clones are picked and DNA from these clones are screened for resistance to digestion by NsiI. Clones having DNA that is not degraded by the endonuclease may harbor insert/vector combinations carrying the NsiI methylase. The NsiI methylase gene is subcloned from the initial clone into a different vector by using the same strategy. Note that the vector must have at least one NsiI site which the methylase may protect during the in vitro NsiI enzymatic digestion selection step.

The resulting clones express NsiI methylase but not NsiI endonuclease. One may then identify clones carrying sequences which overlap and flank the methylase sequences. One maps the clones using a variety of restriction enzymes, and identifies a DNA fragment which is always present in the methylase clones. One uses this fragment as a probe and constructs a hybridization map of the N. sicca chromosome. One then identifies a region which is near the methylase gene in the chromosome but is not present on the initial methylase clones. A DNA fragment in the *N. sicca* chromosome is identified which spans the region used as probe and continues at least 1 kb beyond, into the region not found in the methylase clones. The *N. sicca* chromosome is cleaved with the pair of restriction enzymes that generate this fragment, and the digestion products are separated by electrophoresis. The fragments which are within 1 kb of the target fragment are isolated and cloned. The plasmid library thus generated is screened by analyzing plasmid preparations from individual clones. Cells harboring clones with a fragmentation pattern resembling the desired fragment are then assayed for NsiI endonuclease activity. Clones expressing such activity can be chosen for further work. Note that all of the work with the second library must be done in host cells also harboring and expressing the methylase gene cloned from the first DNA library.

The present invention also encompasses the expression of the desired restriction endonuclease and modification methylase in prokaryotic and eukaryotic cells. Eukaryotic and prokaryotic hosts that may be used for cloning and expressing the enzymes of the invention are well known in the art. Vectors which replicate in such host cells are also well known (Maniatis et al., *Molecular Cloning: A Laboratory Manual*, Cold Spring Harbor Laboratory Press, Cold Spring Harbor, N.Y. (1982)).

Preferred prokaryotic hosts include, but are not limited to, bacteria of the genus Escherichia, Bacillus, Streptomyces, Pseudomonas, Salmonella, Serratia, Caryophanon, etc. The most preferred prokaryotic host is *E. coli*. Bacterial hosts of particular interest in the present invention include *E. coli* K12 and DH10B.

It has been found that *E. coli* has several mechanisms (restriction systems) for identifying foreign DNA and destroying it. This can be a significant problem in cloning experiments, resulting in reduced recovery of the desired sequences. In particular, it has been found that *E. coli* contains restriction systems that degrade DNA when it is methylated, either on cytosine residues or adenine residues. Specifically, the well known methylcytosine-specific systems include mcrA (rglA), and mcrB (rglB) (Revel et at., *Virology* 31:688–701 (1967); Raleigh et al., *Proc. Natl. Acad. Sci. USA* 83:9070–9074 (1986)). The methyladenine-specific restriction system his been designated mrr (Heitman et al., *J. Bacteriol.* 169:3243–3250 (1987)). Thus, the preferred host for cloning and expressing the genes encoding for the enzymes of the present invention are hosts in which these types of restriction systems have been inactivated through mutation or loss.

Once the desired restriction endonuclease and modification genes have been isolated, a number of recombinant DNA strategies exist for enhanced production of the desired protein in eukaryotic or prokaryotic hosts. These strategies, which will be appreciated by those skilled in the art, utilize high copy number cloning vectors, expression vectors, inducible high copy number vectors, etc.

Enhanced production of the restriction endonuclease and modification methylase can be accomplished, for example, by operably linking the desired gene to a strong prokaryotic promoter, although the natural restriction or modification methylase gene promoter may be used. Such well known promoters may be either constitutive or inducible. Examples of constitutive promoters include the int promoter of bacteriophage λ, and the bla promoter of the β-lactamase gene of pBR322, etc. Examples of inducible prokaryotic promoters include the major left and right promoters of bacteriophage λ ($P_L$ and $P_R$, the trp, recA, lacZ, gal, trc, and tac promoters of *E. coli*, the amylase (Ulmanen, I., et al., *J. Bacteriol.* 162:176–182 (1985)), the $\delta^{28}$-specific promoters of *B. subtilis* (Gilman, M. Z., et al., *Gene* 32:11–20 (1984)), the promoters of the bacteriophages of Bacillus (Gryczan, T. J., In: *The Molecular Biology of the Bacilli*, Academic Press, Inc., N.Y. (1982)), and Streptomyces promoters (Ward, J. M., et al., *Mol. Gen. Genet.* 203:468–478 (1986)). Prokaryotic promoters are reviewed by Glick, B. R., (*J. Ind. Microbiol.* 1:277–282 (1987)); Cenatiempo, Y. (*Biochimie* 68:505–516 (1986)); and Gottesman, S. (*Ann. Rev. Genet.* 18:415–442 (1984)).

In order to enhance the production of the desired restriction endonuclease in a prokaryotic cell, it is important to maintain expression of the corresponding modification methylase gene sufficient to protect the DNA of the recombinant host against cleavage with the cloned restriction endonuclease. Therefore, it may be necessary to enhance the level of methylase expression in conjunction with increased endonuclease activity.

Furthermore, those skilled in the art will recognize that various combinations of maintaining both the modification and restriction genes within the same recombinant host can be constructed. The only requirement, when cloning restriction endonuclease genes, is that the recombinant host contain and express the methylase gene corresponding to the endonuclease gene being cloned.

The clones described herein may be improved by sequencing the endonuclease and methylase genes and subcloning each gene in front of suitable promoters with the ribosome binding sites placed in the correct position. The procedures for doing this are well known to those of ordinary skill in the art. In particular, the endonuclease may be under better control it were amplified by PCR using an oligonucleotide which changed the sequence at the amino terminal start site to 5' CAT ATG 3', where ATG is the start codon, and then subcloning the gene into the NdeI site of a vector such as pRE1 and pRE2 (Reddy et al. (1989) *Nucl. Acids Res.* 24:10473–10488). This may optimize expression and control leaky expression at the same time. Other improvements could also be made, such as cloning the endonuclease gene in front of the T7 or other promoters, or cloning the endonuclease gene on a runaway replication plasmid (Hammond, A. W. et al. (1990) *Gene* 97:97–102).

The enzymes of this invention, NsiI and NsiI methylase, or isoschizomers thereof, are preferably produced by fermentation of the recombinant host (prokaryotic or eukaryotic) containing and expressing the cloned restriction endonuclease and/or modification methylase genes. The recombinant host, such as *E. coli*, producing the cloned proteins, can be grown and harvested according to techniques well known in the art.

After culturing, the recombinant host cells of this invention can be separated from the culture liquid, for example, by centrifugation. The modification methylase and/or restriction enzymes produced by this host can be extracted and purified by using known protein purification techniques commonly employed for these types of enzymes.

In general, the collected microbial cells are dispersed in a suitable buffer, and then broken down by ultrasonic treatment to allow extraction of the enzyme by the buffer solution. After removal of the residue by ultracentrifugation, desired enzyme can be purified by extraction, ion-exchange chromatography, molecular-sieve chromatography, affinity chromatography, and the like, giving the restriction endonuclease of this invention.

According to the present invention, assays to detect the presence of the restriction endonucleases and modification methylases can be used during the conventional biochemical purification methods to determine the presence of these enzymes.

The restriction endonuclease can be identified on the basis of the cleavage of its recognition sequence. For example, lambda (λ) DNA can be used as a substrate. After digestion with endonuclease, the DNA fragments are separated electrophoretically in agarose gels in the buffer systems conventional for fragment separation and in the presence of ethidium bromide (EtdBr).

Demonstration of modification methylase activity can be, but is not limited to, a two-step identification process. First, substrate DNA (λ DNA) that contains the recognition sequence is incubated with column fractions to be tested for methylase activity. Second, this DNA is then challenged with the corresponding restriction activity to identify those fractions which contain methylase activity. For example, while assaying for NsiI methylase, the DNA samples will be challenged with NsiI. Thus, DNA samples which do not exhibit cleavage with NsiI contain NsiI methylase activity.

Having now generally described the invention, the same will be more readily understood through reference to the following Examples which are provided by way of illustration, and are not intended to be limiting of the present invention, unless specified.

EXAMPLES

Example 1: Experimental

Example 1.1: Definition of abbreviations

Ad-2, adenovirus-2; Ap, ampicillin; bp, base pair(s); EthBr, ethidium bromide; kbp, 1000 base pairs (bp); IPTG, isopropylthio-beta-galactoside; Km, kanamycin; PolIK, Klenow (large) fragment of $E. coli$ DNA polymerase I; PCR, polymerase chain reaction; $^R$, resistance; $^S$, sensitivity; SDS, sodium dodecyl sulfate; Sp, spectinomycin; Tc, tetracycline; and X-Gal, 5-bromo-4-chloro-3-indolyl-beta-D-galactoside.

Example 1.2: Bacterial Strains and Growth Conditions

*Neisseria sicca* BRL 397 producing NsiI restriction endonuclease was grown in a 14 l fermentor at 30° C. to mid-log phase in BHI (Brain Heart Infusion, Difco, Detroit, Mich.). These cells were centrifuged and stored at 70° C. as a cell pellet before total genomic DNA isolation.

*E. coli* strains were grown at 37° C. in YET broth (5 g/l yeast extract, 10 g/l tryptone, and 5 g/l NaCl with antibiotic supplements of 100 mg/l ampicillin; 20 mg/l tetracycline; and 50 mg/l kanamycin; as appropriate. *E. coli* strain DH10B and DH10B/pSUM83 were used for cloning the NsiI genes. DH10B is a recA1⁻, endA⁻, phi80dlacZdeltaM15 derivative of MC1061 (Casadaban M J and Cohen S N (1980) *J. Mol. Biol.* 138:179–207). Competent *E. coli* strains were either obtained from LTI or made by a protocol described by Hanahan D (1983) *J. Mol. Biol.* 166:557–580. Electrocompetent *E. coli* were obtained from LTI and electroporation was under standard conditions (Smith M D, Jessee J, Jordan J, and Landers T (1990) *Focus* 12:38–40).

Example 1.3: Vectors/Plasmids

Because a methylase protection scheme was to be used to clone NsiI restriction and modification genes, it was necessary to use vectors containing NsiI site(s). The cosmid pCP13 has at least 1 NsiI site located in the kanamycin-resistance determinant (Darzins A and Chakrabarty AM (1984) *J. Bacteriol.* 59:9–18). The plasmid pUC-Kam is a pUC19 derivative in which a kanamycin resistance determinant from Tn903 was inserted in the ScaI site in pUC19 (James Hartley, Life Technologies Inc.). The plasmids pUC19 (Yanisch-Perron C, Veiera J and. Messing J (1985) *Gene* 33:103–119) and pSU39 (*Gene* (1991) 102:73–78) have been described.

Example 1.4: DNA Isolations

Small scale plasmid DNA isolations were performed by an alkaline lysis method (Maniatis T et al. (1982) *Molecular Cloning: a laboratory manual,* Cold Spring Harbor Laboratory, Cold Spring Harbor, N.Y.). For large scale preparations, alkaline lysis was followed by a standard CsCl-ethidium bromide (EthBr) gradient centrifugation.

*N. sicca* total genomic DNA was isolated by resuspending 1 gram of frozen *N. sicca* cells in 15 ml of TES buffer. A 20 mg/ml lysozyme solution in TE buffer was added to the cell suspension to a final concentration of 1 mg/ml. After a 10 min incubation at 23° C., 20 μl of a 5 μg/μl solution of Proteinase K (Boehringer Mannheim) was added. SDS (from a 10% solution) was added to a 1% final concentration and the suspension was incubated in a 50° water bath for 60 min. Lysis was complete. After cell lysis, the lysate was extracted once with phenol, precipitated with isopropanol, and the DNA was resuspended in 10 ml TE-RNase (see below). The resuspended DNA was extracted with phenol:chloroform:isoamyl alcohol (25:24:1), precipitated with ethanol, and the DNA was resuspended in 2 ml TE-RNAse. The preparation was incubated at 37° for 30 min and then stored at 4° C.

Example 1.5: Solutions

TES: 20 mM Tris•HCl, pH 8.0, 50 mM NaCl and 1 mM EDTA (ethylene diamine tetraacetic acid)EDTA. TE:20 mM Tris•HCl, pH 8.0, and 1 mM EDTA. TE-RNAse: TE+1μg/ml ribonuclease A.

Example 1.6: Colony and Southern Hybridization

Southern hybridizations were performed using biotinylated probe and photo-gene detection using the PhotoGene Nucleic Acid Detection System (LTI, Gaithersburg, Md.). Fragments generated by endonuclease digestion of the appropriate plasmid were separated by agarose gel electrophoresis and isolated from agarose gel slices by the Gene-Clean procedure (Bio101 Inc, P.O. Box 2284, La Jolla, Calif. 92038-2284). Fragments were then labeled with biotin by octamer-primed synthesis in the presence of biotinylated nucleotides using the BioPrime DNA Labeling System (LTI).

Example 1.7: Construction of Genomic Libraries

The cosmid library of *N. sicca* genomic DNA was constructed in pCP13. pCP13 DNA was digested with PstI and dephosphorylated using calf intestine alkaline phosphatase at 50° C. (Boehringer Mannheim). Genomic DNA of *N. sicca* was digested partially with PstI. One μg of cosmid vector DNA was ligated with 4 μg of the appropriate chromosomal DNA using 1 unit of T4 DNA ligase in 1×ligase buffer (LTI) overnight at room temperature. One sixth of the ligated DNA was packaged using the BRL Lambda Packaging System and transfected into DH10B. Approximately $10^4$ Tc$^R$ colonies were pooled and an aliquot was inoculated into 500 ml of Circlegrow media (Bio101) containing tetracycline. After a 5 hour growth at 37°, the cells were harvested and plasmid DNA was purified as described above. This plasmid DNA is referred to as library plasmid DNA.

Example 1.8: Selection of Clones Expressing NsiI Methylase

Clones expressing NsiI methylase were selected by digesting 2 μg of plasmid DNA overnight with 50 units of NsiI. The digested DNA was dephosphorylated, extracted with phenol followed by sec-butanol, and ethanol precipitated. One tenth of the digested DNA was used to transform *E. coli* DH10B cells by electroporation. Plasmid DNA isolated from clones selected on plates containing tetracycline (pCP13 vector) or ampicillin (pUC-Kam vector) was tested for resistance to NsiI. Protection of the resident plasmid and the host chromosomal DNA from digestion with NsiI indicated the presence of methylase activity.

Example 1.9: Screening For Clones With NsiI Endonuclease Gene

Selection of NsiI endonuclease clones required the use of a protected host expressing NsiI methylase. *N. sicca* chromosomal DNA was digested with EcoRI and HindIII, and all the fragments between 2 and 3 kb were separated by gel electrophoresis, isolated by the gene clean procedure, and ligated With pUC19 cleaved with EcoRI and HindIII. DH10B/pSUM83 (DH10B cells containing the pSUM83 plasmid) were transformed with the ligation mixture and Ap$^R$ Km$^R$ colonies were tested for the presence of the expected PstI and XbaI sites. Positive clones were subsequently tested in vitro for restriction enzyme activity.

Example 1.9: Assay for Restriction Enzyme

Overnight cultures (20 ml) were harvested and resuspended in 1 ml buffer containing 10 mM Tris•HCl (pH 7.5), 10 mM beta-mercaptoethanol and 1 mM EDTA. Cells were sonicated on ice by three 10 second blasts with a micro-tip probe. Lambda DNA substrate (1.0 µg) was digested in 1×BRL REact™ 3 buffer with serial dilutions of extract for 1 hour at 37° C. DNA was fractionated by electrophoresis and visualized by EthBr staining.

Example 2: Identification of Methylase Clones

Plasmid DNA was isolated from Tc$^R$ clones surviving the NsiI selection procedure on the pCP13 PsiI library. All 12 clones tested expressed methylase as judged by resistance to NsiI restriction of the host DNA. The clones were digested with PstI, and 10 of the 12 appeared to share a 10 kb PstI fragment. It appeared that some other fragments could have been common between some of the clones; but in general the clones did not share other fragments. Two clones, pCPM1 and pCPM4, were tested for NsiI endonuclease activity, but neither of these clones exhibited endonuclease activity.

Example 3: Subcloning and localization of the NsiI Methylase Gene

The NsiI methylase gene could have been anywhere in the 20 to 30 kb inserts in the cosmid clones. We have discovered that the best way to localize methylase genes in a cosmid quickly is to make a library of 2–4 kb fragments from the cosmid which contains the methylase, to perform a methylase selection on the library to isolate clones which produce the methylase, and to compare the inserts in these clones for common features. The 2–4 kb Sau3AI fragments of pCPM1 and pCPM4 released by partial digestion were subcloned into the BamHI site of pUC-Kam. The library thus formed was selected for resistance to NsiI digestion, and several NsiI methylase subclones were obtained, among them pUCKamM1, pKamM2, and pUCKamM6. Surprisingly, all of these clones were identical (later mapping demonstrated that this was likely to be due to the unusually small number of Sau3AI sites in this area of the *N. sicca* genome). None of these clones made NsiI endonuclease. A second method to localize a methylase gene on a cosmid is to compare several cosmids which contain the methylase, and clone specific DNA fragments which are common to all or many of them. The digestion patterns of the cosmid clones indicated that they all shared a 10 kb PstI fragment, but had no other PstI fragments in common. The 10 kb PstI fragment from pCPM1 was cloned into PstI-digested pUC-Kam, forming pUCKamM10. Cells with pUCKamM10 were methylated at the NsiI sites, but did not make NsiI endonuclease. All of the NsiI methylase plasmids in pUCKam were mapped by endonuclease digestion (FIG. 3). It was apparent that they shared insert DNA in the region near one end of the 10 kb PstI fragment. To localize the methylase with more precision, a set of exonuclease III-derived deletions of pUCKamM1 were generated and tested for methylase activity. The results demonstrated that deletion of as little as 300 base pairs from the end of pUCKamM1 insert resulted in the loss of NsiI methylase activity. It was therefore concluded that the methylase gene was very near this end of the PstI fragment.

Example 4: Chromosomal Localization the NsiI Methylase Gene

The *N. sicca* genome contiguous to the NsiI methylase gene was mapped to identify which regions were present or missing in the NsiI methylase cosmid clones. A 400 base pair BamHI-HindIII fragment was identified which was present in all such clones. This fragment was isolated and used as probe (probe "A") in the following experiment. *N. sicca* chromosomal DNA was digested with various restriction enzymes and probed with probe "A". The resulting data was used to construct a hybridization map of the *N. sicca* chromosomal DNA in the NsiI methylase region (FIG. 2). We noted that there is a 2.5 kb EcoRI-HindIII fragment spanning the PstI site where the NsiI endonuclease was thought to be located. The NsiI endonuclease gene was ultimately cloned on this fragment.

It appeared that the three NsiI methylase cosmid clones were accurate clones of that region of the chromosome in the 10 kb PstI fragment which they shared. It was possible that the NsiI endonuclease gene was on the 10 kb PstI fragment, or that it was on the adjacent fragment, or that it was on both fragments, spanning the PstI site. Failure to detect NsiI endonuclease activity in the clones could have been due to a lack of expression of the endonuclease in the *E. coli* host. On the other hand, if the endonuclease gene was present at the PstI site, it was possible that previous attempts to clone both genes on a common insert in pCP13 resulted in the isolation of clones in which the 10 kb PstI fragment was present, thus giving NsiI methylase protection, but the adjacent PstI fragment which was required for NsiI endonuclease expression was missing. We compared several of the NsiI clones to determine if there were any PstI fragments other than the 10 kb PstI fragment which were shared by the clones. One 2.6 kb PstI fragment was identified in 6 of the 12 clones by hybridization (including pCPM4). This 2.6 kb PstI fragment has two SphI sites. If it were contiguous with the end of the 10 kb PstI fragment (the end which has an XbaI site), an XbaI-SphI digest of pCPM1 would contain a 700 base pair fragment which would hybridize to the 2.6 kb PstI probe. Since the only fragments that hybridized were much bigger, it was clear that the 2.6 kb PstI fragment was not contiguous with the 10 kb PstI fragment at the end with the XbaI site (where the methylase gene is). Since there were no other PstI fragments which appeared to be shared by the 12 NsiI methylase cosmid clones, it seemed likely that all or most of them were missing the PstI fragment which was contiguous to the end of the 10 kb PstI fragment where the NsiI methylase was located.

With this data in hand it was still impossible to be sure that the NsiI endonuclease gene was not already cloned, even though it was silent in *E. coli*. Such was the case, for example, in the cloning of HpaII. Prior experience has suggested, however, that cloning a restriction system intact by methylase selection is more likely when the endonuclease is not made in abundance in the original producer in the first place (e.g. PvuI, XmaIII) and less likely when the original producer makes over 20,000 units per gram (e.g. KpnI, ClaI), although there are exceptions to this rule (AluI, HindIII). Since *N. sicca* makes about 40,000 units per gram cells, we hypothesized that the NsiI endonuclease spanned the PstI site near the methylase end of the 10 kb PstI fragment and could not be cloned in one step with the endonuclease. We therefore sought to subclone the NsiI methylase so that we could introduce the NsiI endonuclease gene into a methylase-protected host without killing the recipient cells.

Example 5: Generating a methylase protected host

The 4.5 kb PstI-EcoRI fragment from pUCKamM1 was cloned into the EcoRI-PstI sites of pUC19, forming pUCM33. The 4.5 kb SphI-EcoRI fragment from pUCM33 was cloned into pSU39, forming pSUM83. Since this construction had no NsiI sites, the function of the NsiI methylase gene was checked by introducing pCP13 into the strain which had pSUM83, and digesting the plasmid DNA of the strain with NsiI.

Example 6: Cloning of the NsiI Endonuclease Gene in a Protected Host

The ClaI endonuclease was cloned by using as a probe a DNA sequence that was linked to the methylase gene but not required for methylase expression. In the case of NsiI, the only such sequences that were available were on the side of the methylase distal to the endonuclease gene. Such a sequence could be used as a probe, but the clones could only be expected to contain the endonuclease gene if they also contained the methylase and the probe region. Such a clone would have to be fairly large, such as that found on a cosmid. Consistent with this line of reasoning, a cosmid library was constructed in a host protected by the NsiI methylase, and the library was analyzed by hybridization to a probe specific for the NsiI methylase region but not included in the insert in the methylase protecting plasmid. It was apparent that this library was also re-arranged in the area where the endonuclease gene was suspected to be. This unexpected result could have been because of some unknown toxic gene linked to the NsiI endonuclease, or to the toxicity of the endonuclease gene itself. Thus, the only available probe for colony hybridization called for the use of a cosmid library, but it was apparent that it would be difficult, if not impossible, to isolate a functional NsiI endonuclease gene fragment from a cosmid library (even in a methylase-protected host). An alternate strategy was devised which would not require any further hybridization.

If one makes a digest of a bacterial genome and electrophoreses the fragments in a standard agarose gel, one obtains a large variety of fragments, so many that each individual fragment is barely visible. How many fragments appear in the interval of, say, from 2 to 3 kb depend on the enzyme used for digestion and the G+C content of the bacterial genome, among other things. The number of such fragments in a given interval can be crudely estimated from the proportion of DNA in that interval and the genome size of the bacteria. If 5% of the DNA of a 4,000 kb genome is in that interval, it would mean that there are about 80 fragments in that interval (80×2.5 kb average size=200 kb, which is 5% of 4,000). Note that this calculation is only a very rough estimate, since the genome size of *N. sicca* has not been demonstrated to be 4,000 kb, the amount of DNA in a given interval was only estimated by eye from ethidium bromide fluorescence, and so on. Nevertheless it is apparent that there are only on the order of a hundred fragments in a well-chosen interval. If both HindIII and EcoRI are used to generate the fragments, and if each enzyme cleaves at about the same frequency, it may be expected that only about half of the fragments in the interval are EcoRI-HindIII fragments, and that the others would be EcoRI fragments or HindIII fragments. Therefore, when *N. sicca* DNA is cleaved with EcoRI and HindIII in combination, and the fragments between 2 and 3 kb are cloned in the EcoRI-HindIII gap of a properly prepared vector, it is possible that the library will only contain about 40 distinct fragments. If the desired fragment has a distinctive trait, such as an XbaI site near one end, then it is possible to screen for the desired clone by making the library, isolating plasmid DNA from a series of randomly selected clones, digesting a the plasmid DNA with XbaI and further examining only those with the XbaI site in the insert. Thus a seemingly unworkable proposition, plasmid analysis of random clones from a library, is actually a reasonable approach providing that there is not an easier alternative such as hybridization, that the interval chosen does not contain too high a proportion of the total genomic DNA, that the two enzymes chosen cut at roughly equal frequencies, that the restriction map in the desired region is known with some precision, and some distinguishing trait of the desired clone is known that can be easily tested in a number (e.g., 48) of plasmid preparations.

The restriction map of the *N. sicca* chromosome was scanned for a fragment which fulfilled the above conditions and spanned the PstI site and had enough DNA to encode the endonuclease gene (at least 1 kb) but not much DNA beyond that (no more than 3 kb). Such a fragment was the 2.5 kb EcoRI-HindIII fragment indicated in FIG. 2. The *N. sicca* chromosomal DNA was cleaved with EcoRI and HindIII in combination, and DNA in the 2–3 kb region was excised from the gel, purified by the gene-clean procedure, and cloned into the EcoRI-HindIII sites of pUC19. This ligation mixture was transformed into *E. coli* cells harboring pSUM83 (a plasmid which expresses the NsiI methylase gene). Plasmid DNA from 24 randomly selected clones was cleaved with XbaI, and the 8 clones with an XbaI site were cleaved with PstI. Of these, two clones had the desired properties, and they were apparently identical. Each clone (pUC123 and pUC140) produced over 26,000 units of NsiI endonuclease per gram of cells.

These data may be used by those of ordinary skill in the art to clone the NsiI genes from BRL397 and express them in a heterologous host. The endogenous promoter is highly active in *E. coli* so need not be replaced. The methylase may be cloned without a complete, functional endonuclease gene from pUCM33 by any of several combinations of restriction endonucleases. The data provided in the text and Figures can be used by those of ordinary skill in the art to design a cloning scheme that would isolate the NsiI methylase and endonuclease gene using well known methods of molecular biology and genetic engineering.

*E. coli* DH10B Rec+ (pUC123)(pSUM83) was deposited at the Northern Regional Research Center, 1815 N. University St., Peoria, Ill. 61604, on Oct. 21, 1993 as NRRL B-21151.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following Claims.

What is claimed is:

1. A method of producing NsiI restriction endonuclease comprising:
   (a) growing a recombinant host cell which is protected from NsiI cleavage and which comprises a structural gene coding for the NsiI restriction endonuclease under conditions suitable for the expression of said endonuclease; and
   (b) isolating said NsiI endonuclease.

2. The method of claim 1, wherein said structural gene is obtainable from *Neisseria sicca* BKL 397 which is on deposit as ATCC 29256.

3. The method of claim 1, wherein said recombinant host cell is *E. coli* DH10B Rec$^+$(pUC123)(pSUM83) which is on deposit as NRRL B-21151.

4. The method of claim 1, further comprising the step of purifying said NsiI restriction endonuclease.

5. The method of claim 1, wherein said structural gene coding for the NsiI restriction endonuclease is contained in a vector.

6. The method of claim 5, further comprising the step of purifying said NsiI restriction endonuclease.

7. The method of claim 1, wherein said host cell contains a first and a second DNA molecule, wherein
   (a) the first DNA molecule comprises a structural gene coding for said NsiI restriction endonuclease operably linked to a promoter, wherein said structural gene is expressed under control of the promoter; and
   (b) the second DNA molecule comprises a NsiI restriction modification methylase gene, wherein the methylase gene is capable of protecting DNA contained in said host cell from degradation by NsiI endonuclease.

8. The method of claim 7, wherein said first DNA molecule and said second DNA molecule are different.

9. The method of claim 7, wherein said first DNA molecule and said second DNA molecule are the same molecule.

10. The method of claim 7, wherein said promoter is an NsiI endonuclease gene promoter.

11. The method of claim 7, wherein said first DNA molecule is contained in a vector and said second DNA molecule is contained in a different vector from said vector.

12. The method of claim 7, wherein said first DNA molecule and said second DNA molecule are contained in the same vector.

13. The method of claim 11, farther comprising the step of purifying said NsiI restriction endonuclease.

14. The method of claim 12, further comprising the step of purifying said NsiI restriction endonuclease.

15. A method of using a vector comprising a structural gene coding for the NsiI restriction endonuclease, to prepare an NsiI restriction endonuclease, said method comprising:
   (a) introducing said vector into a host cell to produce a recombinant host cell;
   (b) culturing said recombinant host cell; and
   (c) isolating said restriction endonuclease from said recombinant host cell.

* * * * *